Figure 1:
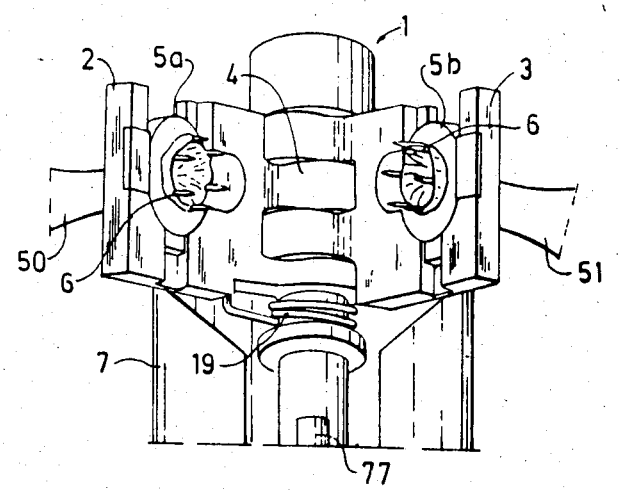

United States Patent [19]

Berggren et al.

[11] Patent Number: 4,607,637

[45] Date of Patent: Aug. 26, 1986

[54] SURGICAL INSTRUMENT FOR PERFORMING ANASTOMOSIS WITH THE AID OF RING-LIKE FASTENING ELEMENTS AND THE FASTENING ELEMENTS FOR PERFORMING ANASTOMOSIS

[76] Inventors: Anders Berggren, Bergdalsgatan 6, 582 45 Linköping; Håkan Rohman, Vitsippestigen 4, 590 20 Mantorp; Leif Östrup, Onkel Adamsgatan 10, 582 35 Linköping, all of Sweden

[21] Appl. No.: 516,462

[22] Filed: Jul. 22, 1983

[51] Int. Cl.$^4$ ............................................. A61B 17/11
[52] U.S. Cl. ................................................ 128/334 C
[58] Field of Search ............... 128/334 C, 334 R, 346, 128/335

[56] References Cited

U.S. PATENT DOCUMENTS

| | | |
|---|---|---|
| 1,151,300 | 8/1915 | Soresi . |
| 1,918,890 | 7/1933 | Bacon . |
| 2,434,030 | 1/1948 | Yeomans ............................ 128/346 |
| 2,453,056 | 11/1948 | Zack .................................... 128/334 |
| 2,638,901 | 5/1953 | Sugarbaker ........................ 128/334 |
| 3,254,650 | 6/1966 | Collito ................................ 128/334 |
| 3,254,651 | 6/1966 | Collito ................................ 128/334 |
| 3,258,012 | 6/1962 | Nakayama et al. ................ 128/334 |
| 3,265,069 | 8/1966 | Healey, Jr. et al. ................ 128/334 |
| 3,316,914 | 5/1967 | Collito ................................ 128/334 |
| 3,409,914 | 11/1968 | Jones . |
| 3,456,965 | 7/1969 | Gajewski et al. .................. 285/260 |
| 3,484,121 | 12/1969 | Quinton .............................. 285/242 |
| 3,514,791 | 6/1970 | Sparks ................................ 3/1 |
| 3,552,626 | 1/1971 | Astafiev ............................. 227/76 |
| 3,561,448 | 2/1971 | Peternel ............................. 128/334 |
| 3,606,808 | 9/1971 | Bowden ............................. 82/40 |
| 3,628,813 | 12/1971 | Lee et al. ............................ 285/31 |
| 3,683,926 | 8/1972 | Suzuki ................................ 128/334 |
| 3,713,441 | 1/1973 | Thomas .......................... 128/214 R |
| 3,742,933 | 7/1973 | Bucalo ............................... 128/1 R |
| 3,771,526 | 11/1973 | Rudie ................................ 128/334 |
| 3,774,615 | 11/1973 | Lim et al. ........................... 128/334 |
| 3,831,584 | 8/1974 | Bucalo ............................... 128/1 R |
| 3,833,940 | 9/1974 | Hartenbach ....................... 128/334 |
| 3,877,435 | 4/1975 | Bucalo ............................... 128/334 |

(List continued on next page.)

FOREIGN PATENT DOCUMENTS

| | | |
|---|---|---|
| 899749 | 5/1972 | Canada ............................... 128/122 |
| 908529 | 8/1972 | Canada ............................... 128/122 |
| 1057729 | 5/1959 | Fed. Rep. of Germany . |
| 2101282 | 7/1972 | Fed. Rep. of Germany . |
| 2200981 | 7/1973 | Fed. Rep. of Germany . |
| 2600142 | 7/1977 | Fed. Rep. of Germany . |
| 2657255 | 6/1978 | Fed. Rep. of Germany . |
| 2316910 | of 0000 | France . |
| WO82/01644 | 5/1982 | PCT Int'l Appl. . |

OTHER PUBLICATIONS

Holt et al., "A New Technique for End-to-End Anastomosis of Small Arteries", Surgical Forum 11:242 (1960).
Nakayama et al., "A Simple New Apparatus for Small Vessel Anastomosis (Free Autograft of the Sigmoid Included)", Surgery, vol. 52, No. 6, pp. 918–931 (Dec. 1962).

Primary Examiner—Michael H. Thaler
Attorney, Agent, or Firm—Woodcock Washburn Kurtz Mackiewicz & Norris

[57] ABSTRACT

In surgery, especially in microsurgery, the joining of blood vessel ends or other tubular organs, anastomosis, consumes a considerable part of the time. In order to carry out anastomosis rapidly and reliably a surgical instrument (1) according to the invention is provided with two clamping members (2,3), each being arranged to support a fastening structure (5a,5b) comprising a ring with axially directed pins (6). The clamping members (2,3) are rotatably connected to the instrument and can be actuated by a mechanism (i.a. 7) to be turned towards each other to join the fastening structure (5a,5b) and vessels or organs (50,51) threaded onto these.

The invention also relates to fastening devices (5a,5b) shaped in such a manner that they are retained in the clamping means (2,3) of the instrument until the joining has taken place.

4 Claims, 6 Drawing Figures

U.S. PATENT DOCUMENTS

| | | | |
|---|---|---|---|
| 3,880,137 | 4/1975 | Bucalo | 128/1 R |
| 3,882,862 | 5/1975 | Berend | 128/214 R |
| 3,908,662 | 9/1975 | Razgulov et al. | 128/334 |
| 3,945,052 | 3/1976 | Liebig | 3/1 |
| 3,974,835 | 8/1976 | Hardy | 128/334 |
| 3,990,434 | 11/1976 | Free | 128/1 R |
| 4,055,186 | 10/1977 | Leveen | 128/334 |
| 4,198,982 | 4/1980 | Fortner et al. | 128/334 |
| 4,200,107 | 4/1980 | Reid | |
| 4,214,586 | 7/1980 | Mericle | 128/334 |
| 4,289,133 | 9/1981 | Rothfuss | 128/334 |
| 4,294,255 | 10/1981 | Geroc | 128/334 |
| 4,306,545 | 12/1981 | Ivan et al. | 128/1 R |
| 4,331,150 | 5/1982 | Braun et al. | 128/334 C |
| 4,350,160 | 9/1982 | Kolesov et al. | 128/334 |
| 4,467,802 | 8/1984 | Maslanka | 128/321 |

SURGICAL INSTRUMENT FOR PERFORMING ANASTOMOSIS WITH THE AID OF RING-LIKE FASTENING ELEMENTS AND THE FASTENING ELEMENTS FOR PERFORMING ANASTOMOSIS

The present invention relates to a surgical instrument for joining two vessel ends or other tubular organs and establishing liquid connection between them, i.e. anastomosis, with the aid of annular clamping devices, oriented in an axial direction, on which the vessel ends are threaded before the joining. The invention also relates to anastomosis rings to be used in anastomosis with this surgical instrument. The instrument and the anastomosis rings are shaped and adapted to be utilized mainly in microsurgery.

From the U.S. Pat. No. 3,258,012, Nakayama, et al., it is previously known to join two blood vessel ends by means of a pair of needle discs having alternately spaced projecting needles and holes for these on an annular base element. For the joining of two blood vessel ends by means of these needle discs or anastomosis rings, two forceps are used, retaining the needle disc during threading of the blood vessel end into the needles and holding the needle disc in a suitable position, so that, it can be secured to the needle disc on the other vessel end, by the needles being pressed through the holes on the opposite needle disc and bent when the guided forceps are pressed together.

One difficulty in using Nakayama's method is that two different separate forceps are needed to perform the anastomosis. The guides in these two forceps are to be fitted into each other before the two forceps are pressed together by means of a third instrument. Another difficulty may arise, since the tips of the blades of the two anastomosis forceps which carry, among other things, one of the guides, because they extend considerably distance from its associated needle disc which extension may create problems when the surgical area is limited.

Another difficulty in the known method is that the needles of the needle discs are intended to be bent around the opposite needle disc, since they are relatively long. During operations on vessels with small dimensions they will be easily exposed to bending and misalignment during the handling and the threading of the ends of the blood vessel, and a malfunction may be the result due to the fact that during the pressing together all needles are not brought through the correct hole in the opposite needle disc.

Said difficulties are overcome effectively by means of an instrument and anastomosis rings according to the invention. Thus, one object of the invention is to provide a surgical instrument which retains two anastomosis rings during the threading of the vessel ends and shaped so that the anastomosis rings are directed towards each other and that the instruments, moreover, comprises means for pressing the anastomosis rings together without the need for any additional tools or instruments.

It is also an object of the invention to provide anastomosis rings being adapted to the surgical instrument according to the invention.

Another object of the invention is to achieve an anastomosis instrument and anastomosis rings being adapted for the joining of vessels having small dimensions and in surgical areas having limited space.

These and other objects are met by means of an anastomosis instrument and anastomosis rings having the characterizing features defined in the claims.

Figure 2:
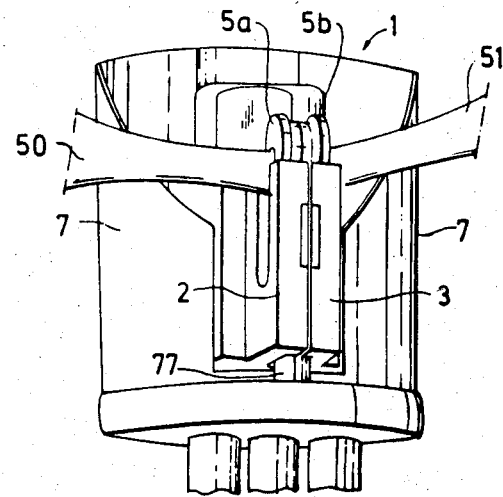
Figure 4:
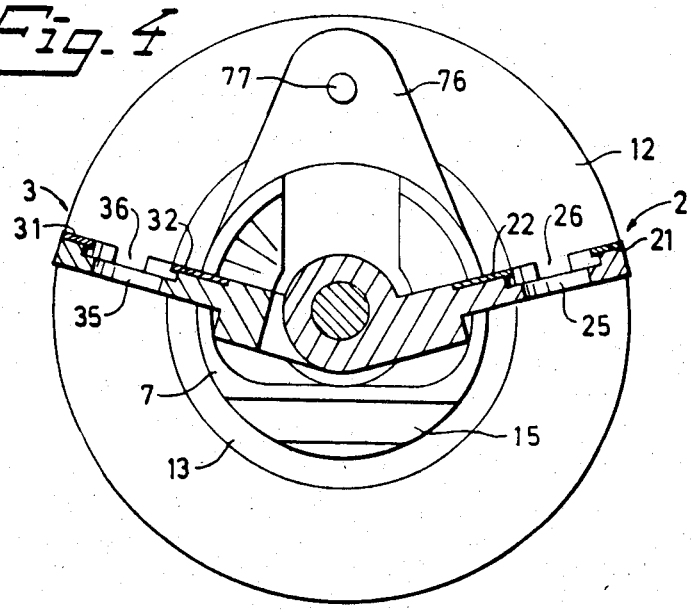
Figure 5:
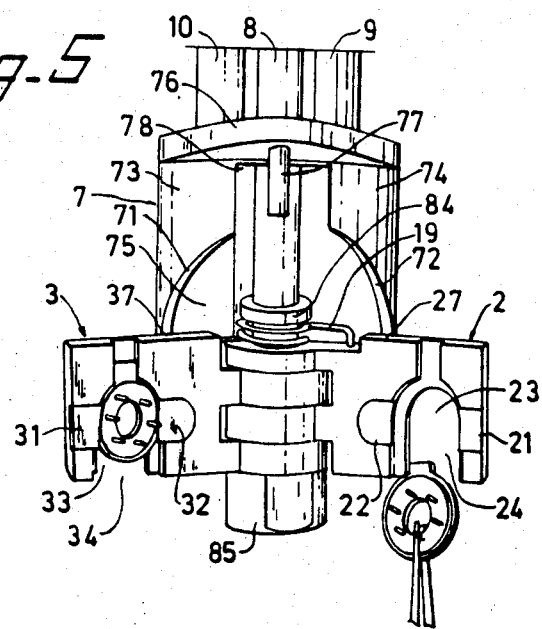

The invention will be described in more detail in connection with the embodiments shown in the drawings, where FIG. 1 shows an enlarged portion of an instrument according to the invention during one moment of the sequences of its operation, FIG. 2 shows the same part of the instrument as FIG. 1 at a later sequence, FIG. 3. shows an enlargement, partly in section, of the whole instrument of FIGS. 1 and 2 with a central portion removed, FIG. 4. shows a further enlargement of the section IV-IV in FIG. 3, FIG. 5. shows enlarged parts of the front part of the instrument, and FIG. 6. shows an enlargement with high magnification of an embodiment of a fastening devices according to the invention.

FIGS. 1 and 2 have the object to illustrate the utilization of a surgical instrument according to the invention in the joining of two vessels with fastening means according to the invention. FIGS. 1 and 2 show only those parts of the instrument 1 forming the end of the instrument which is used in the surgical area. Thus, the instrument 1 is provided with two clamping means 2,3 which by the aid of a hinge 4 are rotatable around a longitudinal axis of the instrument. According to the invention each clamping means supports a fastening means 5a, 5b. In a position of the clamping means 2,3, where these have been turned apart almost 180° in the hinge, the ends of the blood vessels 50 and 51 have been threaded from below through the center holes of the fastening means 5a and 5b and unfolded and threaded onto the pins 6 of the fastening means. By the actuation of a mechanism the guide bushing 7 is moved lengthwise in the instrument, so that, the clamping means 2,3 are turned towards each other. The clamping means 2,3 move through a position as shown in FIG. 1 before the complete clamping together of the fastening means 5a,5b which are supported by the clamping means 2,3. The pins 6 of the fastening means are then engaged with the corresponding holes in the opposite fastening means. When the guide bushing 7 is further displaced a pusher 77 connected to the guide bushing will push the joined fastening elements 5a,5b and the vessels 50,51 out of the joined clamping means 2,3, as shown in FIG. 2.

Figure 3:
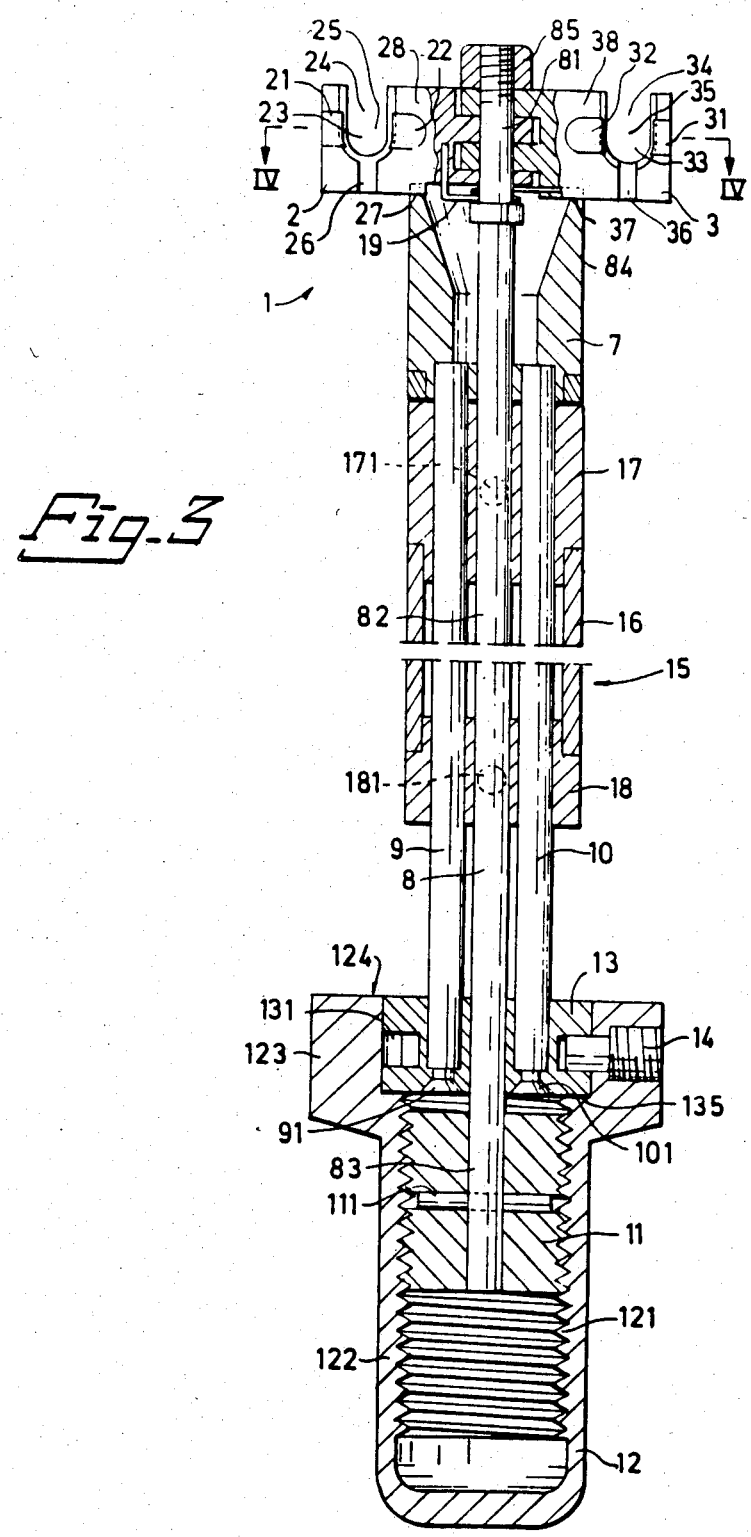

As is apparent from FIG. 3, the clamping means 2,3 are rotatable around a carrier rod 8 at its front end 81. Said rod is parallel to the longitudinal axis of the instrument. A longitudinal handle 15, comprising a tubular casing 16 sealed with end portions 17,18, is attached to the central portion 82 of the carrier rod. The carrier rod 8 passes through central bores in the end portions 17 and 18 and is fixed to these by stop screws 171,181. A carrier 11 is fixed by means of tubular pin 111 through a diametrical hole in the rear end 83 of the carrier rod 8. The carrier 11 comprises a cylindrical body with threads on the cylindrical surface, a hole through the center receiving the carrier rod 8 and a diametrical hole adapted to the tubular rod 111. The thread of the carrier 11 engages the internal thread 121 of a capped nut 12, which comprises a rear cylindrical portion 122 with gripping surfaces around the cylindrical surface, and a front cylindrical portion 123 having a larger outside diameter and a greater material thickness. The capped nut is internally threaded in the main portion of its length, except for a portion at the front end surface 124 of the capped nut where the capped nut has an unthreaded portion with a larger inside diameter which is adapted to a guide 13 of a substantially circular-cylindrical form so that the guide 13 is completely recessed into the front end surface 124 of the capped nut 12. There is an annular groove 131 in the cylindrical surface of the guide 13, in which pin screws 14, screwed radially into the front portion 123 of the capped nut, are arranged to run. The guide 13 is provided with a central hole through which the carrier rod 8 is movably arranged, and on both sides of the central hole other holes are arranged, through which two guide rods 9 and 10 parallel with the carrier rod are fixed to the guide 13 by means of screws 91 and 101. An insert 135 in the form of a washer is arranged in the capped nut 12 against the interior end surface of the guide 13. The guide rods 9 10 run through holes in the end portions 17 and 18 of the handle 15 and the front ends of the guide rods are fixed in the guide bushing 7. A displacement mechanism of the guide bushing 7 is formed by the carrier rod 8, the guide rods 9 and 10, the carrier 11, the capped nut 12, the guide 13 and the pin screw 14, which mechanism moves the guide bushing 7 longitudinally in the instrument when the capped nut 12 is turned.

The guide bushing 7 (FIG. 5) is formed with two curved portions 73 and 74, the outer surfaces of which form parts of a cylinder having the same central axis as the carrier rod 8. The two curved portions 73 and 74 are connected with a substantially flat bottom portion 75 under the carrier rod 8 and a substantially flat end portion 78 against the handle 15 of the instrument. The curved portions of the guide bushing 7 are bevel cut at a sharp angle, preferably about 45° to the central axis, to form guide surfaces 71 and 72, on which the fixing members 3 and 2, respectively, abut with guide surfaces 37 and 27, respectively, under the influence of the torsion spring 19. An end piece 76 is arranged at the end portion 78 of the guide bushing 7, said end piece 76 projecting above the curved portions 73 and 74 of the guide bushing. On the end piece is mounted a pusher 77 in the form of a cylindrical pin directed to the front end of the instrument.

The two fixing members 2 and 3 are each made of a plate 28, 38 provided with a pair of annular elements, the annular elements from the two clamping means being alternately threaded onto the front end 81 of the carrier rod 8 so that a hinge is formed by the two clamping means and the carrier rod. In order to keep the clamping means in position together with the torsion spring 19, the carrier rod is provided with a fixed ring 84 spaced from the front end 81 and a nut 85 screwed onto the end. The two plates 28 and 38 are mirror images of each other. They have substantially flat upper surfaces, the extentions of which intersect along or close to the central line of the carrier rod 8. Each plate 28,38 has at its upper surface a recess 23,33 in which a clamping means can be placed so that it is countersunk in the plate with essentially all of its ring. The recess 23,33 is substantially a cylindrical recess with an opening 24,34 against the front end of the plate in the whole diameter width, so that a clamping means can be pushed in along the plane of the plate.

Stop means 21, 22, 31, 32 are arranged in the inserted position of the ring on both sides of the ring, which stop means are recessed into the upper surfaces of the plates and project somewhat beyond the recess 23,33 so that they cooperate with shoulders on the fastening means and maintain these in position for connection. Below the recesses 23,33 and their openings 24,34, the plates are formed with an additional recess 25,35 through the plate material with a smaller diameter and width but sufficient for the vessel dimension. Moreover, there are grooves 26,36 extending away from the recesses 23 and 33 being adapted to guide means on the fastening means.

Figure 6:
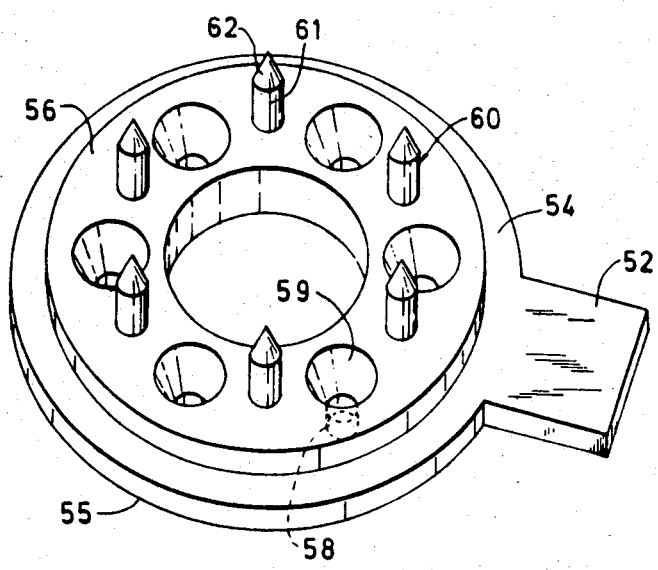

One embodiment of a fastening means of the invention is apparent from FIG. 6. The fastening means comprises a ring 53 with a number of axially directed pins 6 and intermediate holes 58 distributed on a circumference around the center of the ring. The ring 53 has a lower end surface 55 and an upper end surface 56, which are plane-parallel, and the axial pins are secured to the ring and extend through the upper end surface 56. The ring 53 has a central hole through which the vessel end to be joined can be brought and the periphery of the ring forms the main portion of a circular cylindrical surface. A guide element 52 directed radially outwards extends from the periphery of the ring. The central line of the guide element is preferably directed so that it divides the angle between a pin and a hole into equal parts, and in this way the pins in rings with pins in the same direction are correctly guided when joined. A shoulder 54 parallel to the end surfaces of the ring is arranged along the periphery of the ring at a definite distance from the lower end surface 55. In the embodiment shown, the shoulder 54 is arranged around the whole ring but can also be arranged only at certain portions of the ring, at least two diametrically opposed portions being provided with a shoulder. The holes 58 of the ring are preferably shaped with a conically extended portion 59 at the upper end surface 56 in order to guide the pins 6 into the holes 58. The pins 6 of the fastening means has a portion 61 of a substantially equal diameter and a conical tip 62. The portion 61 of the pin having equal diameter extends outside the upper end surface 56 of the ring at least for a distance being equal to and preferably somewhat more than the thickness of the ring. The holes 58 of the ring are adapted to the dimension of the portion 61 of the pins having an equal diameter so that pins forced into the holes 58 are steadily maintained therein. The pins are preferably secured in the ring by casting.

The instrument according to the invention is made so that sterilization thereof easily can be performed. The fastening means are made of a biocompatible material which can be sterilized and does not cause any rejection reactions. The pins of the fastening means are preferably made of stainless steel and the ring of a tissue harmless plastic material such as high density polyethylene.

The embodiments described above are only examples of an instrument and a fastening means according to the invention, which is restricted only by the claims.

We claim:

1. A surgical instrument for joining blood vessel ends or ends of other tubular organs and establishing liquid connection between them, i.e., anastomosis, by means of fastening means comprising connectable rings, said instrument comprising at least two clamping means with stop means for each fastening means, said clamping means being rotatably connected to the instrument and being actuatable by a mechanism for being turned towards each other, said mechanism further comprising a guide bushing which is longitudinally movable along the instrument, said guide bushing being provided with guide surfaces arranged at an angle which is sharp with respect to the longitudinal axis of the instrument, said guide surfaces of the guide bushing cooperating with guide surfaces on corresponding ones of said clamping means so that said clamping means are turned towards each other when the guide bushing is moved towards said clamping means, said guide bushing further comprising a pushing-out element which, upon continued displacement of the guide bushing, actuates the fastening means through grooves in the clamping means so that they are pushed out of the instrument together with the connected the vessels after the guide bushing has turned the clamping means so that the fastening mens are connected to each other.

2. An instrument according to claim 1, wherein each of said two clamping means defines a recess for receiving a ring of said fastening means, the recess having at at least two dimetrically opposed positions stop means extending inwardly towards the recess for positioning said fastening means.

3. An instrument according to claim 2, wherein the recess extends parallel to the longitudinal axis of the instrument to permit insertion of at a portion of said fastening means beyond the stop means of its corresponding clamping means.

4. An instrument according to claim 1, wherein the rotary motion of the clamping means is performed around a front end of a carrier rod forming the logntiudinal axis of the instrument, said instrument further comprising a longitudinal handle attached along the central portion of the carrier rod, said handle comprising a tubular casing with sealing end portions, said instrument further comprising a carrier fixed to the rear end of the carrier rod, said carrier having an external thread engaging the internal thread of a capped nut, said nut being provided with pin screws running in an annular groove in a guide with a central hole movable on the carrier rod, a guide rod being attached to the guide on both sides of the carrier rod, said rod running in holes through the handle and being connected to the guide bushing at the front end of the instrument, and a torsion spring being pre-stretched to turn the clamping means away from each other to make contact with the guide surface of the guide bushing.

* * * * *

UNITED STATES PATENT AND TRADEMARK OFFICE
CERTIFICATE OF CORRECTION

PATENT NO. : 4,607,637

DATED : August 26, 1986

INVENTOR(S) : BERGGREN et al

It is certified that error appears in the above-identified patent and that said Letters Patent is hereby corrected as shown below:

Column 3, line 59, please delete "mcans" and substitute therefor --means--.

In claim 2, column 5, line 17, please delete "dimetrically" and substitute therefor --diametrically--.

In claim 4, column 6, lines 5 and 6, please delete "logntiudinal" and substitute therefor --longitudinal--.

Signed and Sealed this

Twentieth Day of January, 1987

Attest:

DONALD J. QUIGG

Attesting Officer

Commissioner of Patents and Trademarks